(12) United States Patent
Lenker

(10) Patent No.: US 6,746,439 B2
(45) Date of Patent: Jun. 8, 2004

(54) METHOD AND APPARATUS FOR FLUID ADMINISTRATION WITH DISTRIBUTED HEATING

(76) Inventor: Jay Alan Lenker, 408 Panorama Dr., Laguna Beach, CA (US) 92651

( * ) Notice: Subject to any disclaimer, the term of this patent is extended or adjusted under 35 U.S.C. 154(b) by 217 days.

(21) Appl. No.: 09/838,902

(22) Filed: Apr. 19, 2001

(65) Prior Publication Data
US 2002/0156451 A1 Oct. 24, 2002

(51) Int. Cl.$^7$ .............................................. A61M 31/00
(52) U.S. Cl. .................. 604/500; 606/27; 607/113
(58) Field of Search ................. 604/500, 114, 604/113, 101.05, 523; 607/96, 113, 115; 606/27

(56) References Cited

U.S. PATENT DOCUMENTS

| | | | |
|---|---|---|---|
| 4,038,519 A | * | 7/1977 | Foucras .................. 392/472 |
| 4,314,143 A | | 2/1982 | Bilstad et al. |
| 4,464,563 A | | 8/1984 | Jewett |
| 4,759,749 A | * | 7/1988 | Verkaart .................. 604/113 |
| 4,772,778 A | | 9/1988 | Ogawa |
| 5,106,373 A | | 4/1992 | Augustine et al. |
| 5,108,372 A | | 4/1992 | Swenson |
| 5,195,976 A | | 3/1993 | Swenson |
| 5,245,693 A | | 9/1993 | Ford et al. |
| 5,381,510 A | | 1/1995 | Ford et al. |
| 5,408,577 A | | 4/1995 | Weber, Jr. et al. |
| 5,601,894 A | | 2/1997 | Maruschak |
| 5,624,392 A | * | 4/1997 | Saab ........................ 604/43 |
| 5,730,720 A | * | 3/1998 | Sites et al. ................. 604/27 |
| 5,944,660 A | | 8/1999 | Kimball et al. |
| 6,074,363 A | | 6/2000 | Beran et al. |
| 6,142,974 A | | 11/2000 | Kistner et al. |
| 6,175,688 B1 | | 1/2001 | Cassidy et al. |
| 6,236,809 B1 | | 5/2001 | Cassidy et al. |
| 6,530,946 B1 | * | 3/2003 | Noda et al. ............... 607/113 |
| 6,610,083 B2 | * | 8/2003 | Keller et al. ............. 607/105 |

* cited by examiner

Primary Examiner—Edward K. Look
Assistant Examiner—Thor Campbell

(57) ABSTRACT

Disclosure is provided for apparatus and methods to control the temperature of fluids being administered to patients. The apparatus consists of an I.V. reservoir, fluid administration or I.V. tubing, an in-line heater, a heater controller, a temperature sensor located near the patient and feedback circuit connecting the temperature sensor to the heater controller. A method is disclosed which provides for overheating of the fluid so that it cools down to the desired temperature (usually body temperature) by the time it reaches the patient.

In another embodiment, apparatus is disclosed for providing distributed heat to fluids being administered to patients. This apparatus includes heating channels or elements running along a length of the fluid administration tubing. These heating elements are controlled by a controller, which is attached to a temperature sensor, preferably located near the patient. The key advantages of this system include low cost, ease of use and reduced overheating of fluids prior to delivery to the patient. Such overheating could result in degradation of the fluids being delivered to the patient.

14 Claims, 8 Drawing Sheets

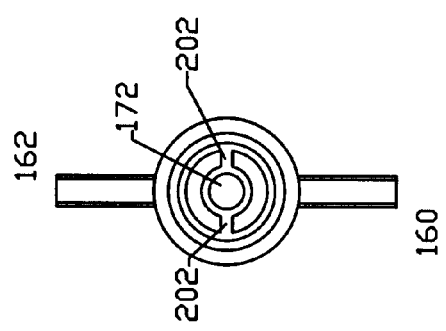
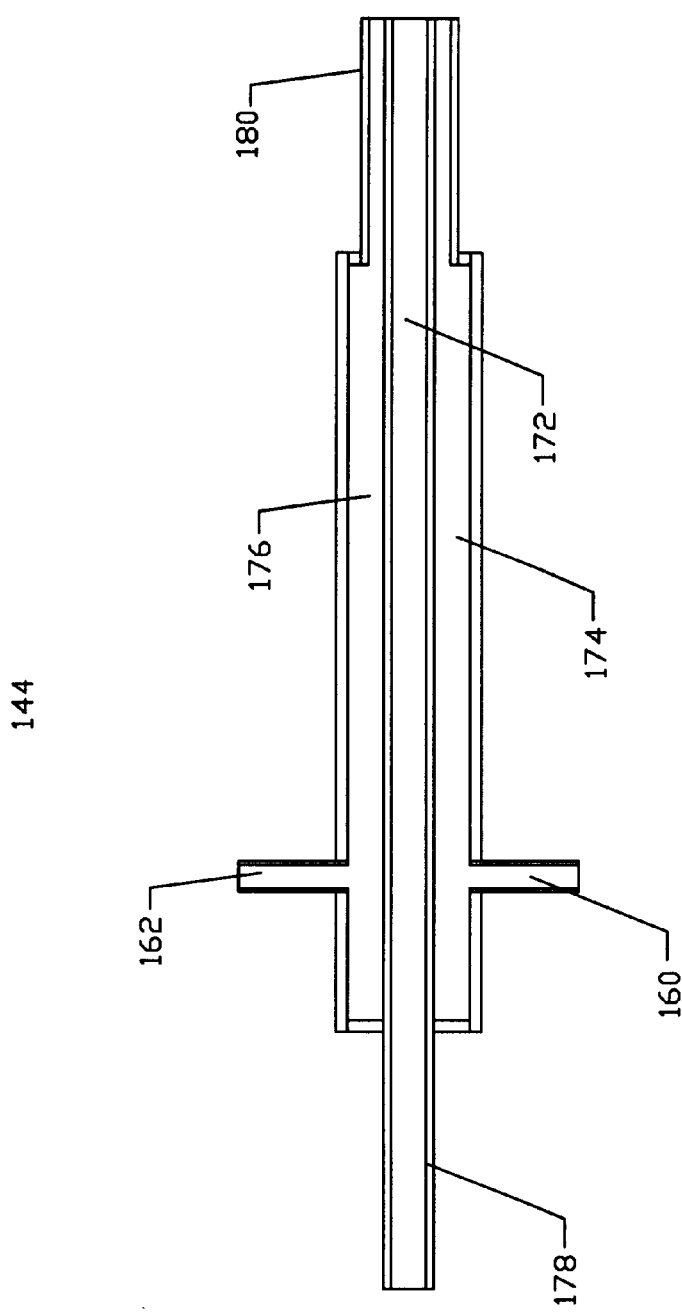
Figure 5A
Figure 5B

METHOD AND APPARATUS FOR FLUID ADMINISTRATION WITH DISTRIBUTED HEATING

FIELD OF THE INVENTION

This invention relates to improvements in devices to control the temperature of fluids administered to patients.

BACKGROUND OF THE INVENTION

Patients often require administration of fluid and blood products at or near body temperature in order to prevent hypothermia from occurring. Such fluid administration is also known as intravenous (I.V.) fluid administration. This is especially important during anesthesia, surgery, shock and trauma when body temperature may be reduced by exposure or by interference with the body's thermoregulatory mechanisms. Hypothermic patients often experience uncontrolled shivering. Patient recovery is often complicated and extended by hypothermia.

Patients requiring blood are often in a state of circulatory shock. Blood is generally delivered from blood banks cold and is typically not adequately warmed to body temperature prior to administration due to time limitations of emergency circumstances. This situation compounds the problems facing the patient. Patient mortality and morbidity could be substantially reduced by delivery of blood and other fluids at proper body temperature.

Current methods of controlling the temperature of intravenous fluids and blood are in-line fluid warmers and external bulk fluid warmers. In-line fluid warmers heat fluids by applying heat directly, using a heating element, to fluid as it passes from the fluid reservoir to the patient. These heaters are located a substantial distance from the patient and temperature loss is substantial by the time the fluid reaches the patient.

External bulk fluid warmers heat the I.V. fluid bottle or bag prior to administration to the patient. The bottles or bags are removed from the heaters and placed next to the patient on an I.V. stand as they are needed. The bottle or bag is attached to a fluid administration set, consisting of a drip chamber, fluid administration (I.V.) tubing, roller clamps and I.V. cannula. The fluid passes from the reservoir to the patient through the fluid administration set under the force of gravity. As the fluid passes through the administration set, it loses heat. This temperature attenuation is exacerbated by low flow rates because of increased fluid dwell time in the I.V. tubing. Because of its long length and corresponding large surface area, substantial heat loss to the room occurs in the I.V. tubing. In addition, the warm fluid bag or bottle cools down over time and will, given enough time, eventually reach ambient room temperature.

Although insulated lines help the problem, temperature losses remain substantial. Typical warming systems are cumbersome, bulky and not sufficiently user-friendly for frequent use. The limitations of existing technology force clinicians to deliver cool and unregulated intravenous fluids and blood to their patients. Although not a preferred practice, there is no convenient method for regulating the temperature and delivery of intravenous fluids and blood products to patients.

SUMMARY OF THE INVENTION

The present invention discloses an improved device and method for controlling the temperature of fluids delivered to a patient. The invention is a system that ensures that fluids delivered to the patient reach the patient at the desired temperature, generally body temperature or 37.0 degrees centigrade.

A temperature measurement probe is located at the end of the I.V. tubing nearest the patient. This temperature measurement is taken near the patient and the information is fed back through wires or by wireless methods to a circuit that controls an in-line heating element that heats the fluid. In this way, temperature losses in the I.V. tubing may be compensated by overheating the fluid so that it reaches the patient at the desired temperature.

In another embodiment of the invention, the feedback from the temperature probe is transmitted through wires, which are integral to the I.V. tubing. The transmission line wires may be embedded or co-extruded, for example, within the tubing. A connector is attached to the transmission line wires in the tubing. This connector allows transmission of information to the controller through electrical leads, attached to the connector. In this manner, cost is reduced and the system is simplified so that no additional components need be set up by the nurse or medical practitioner.

In yet another embodiment, insulated tubing may be used to minimize heat loss in the I.V. tubing and, thus, minimize the amount of overheating required of the in-line heater.

In the preferred embodiment, the in-line heating is accomplished by pumping heated fluid through channels or lumens that run parallel and adjacent to the fluid administration channel in the I.V. tubing. In this way, the heating is distributed along the length of the I.V. tubing so temperature gradients are reduced. This embodiment requires a fluid pump, heater, controller, and temperature probe as well as heat exchange tubing, a heating manifold and at least one fluid shunt.

In yet a further preferred embodiment, the heating channels are located radially exterior to the fluid administration channel. In this way, the heating channels not only heat, but they also buffer, or insulate, the fluid administration channel from ambient temperatures surrounding the I.V. tubing.

In another embodiment, the heating channels, manifold, shunt and delivery tubing are pre-filled with heat exchange fluid so that messy filling and handling are not required.

In yet another preferred embodiment, an additional insulation layer may be disposed radially outward of the heating channels to minimize heat loss to the environment.

In yet another embodiment, the distributed heating is accomplished by resistive or Ohmic heating of a metal or ceramic element that runs along the length of the I.V. tubing.

A key advantage of this system is that fragile fluids such as blood and blood products are not overheated prior to delivery to the patient. Another advantage of the system is that it may be inexpensively fabricated and it may be provided in a convenient configuration that encourages its use. The set allows for disposability, pre-sterilization, low cost and convenient operation.

BRIEF DESCRIPTION OF THE DRAWINGS

FIG. 5A shows a longitudinal cross-section of a heating manifold, which is attached to the distributed heat exchange fluid administration tubing.

FIG. 5B shows a lateral cross-section of a heating manifold, which is attached to the distributed heat exchange fluid administration tubing.

DETAILED DESCRIPTION OF THE INVENTION

The invention herein described is a fluid administration system that heats the fluids and ensures the fluids are delivered to the patient at the desired temperature, typically normal body temperature.

Figure 1:
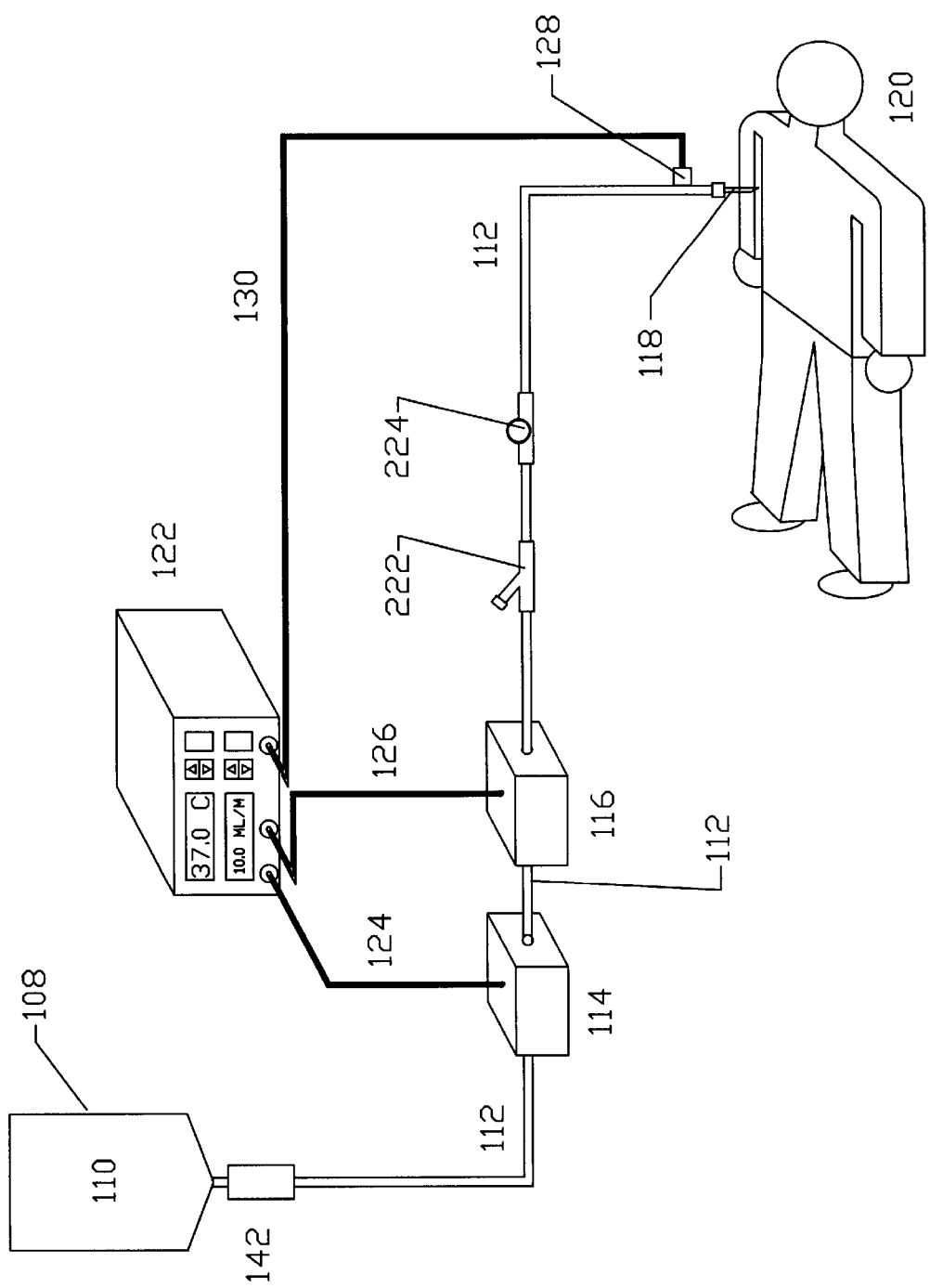
FIG. 1 shows a system for fluid administration utilizing the temperature monitoring and control elements of the invention.

FIG. 1 illustrates one embodiment of a fluid administration system of the present invention comprising a fluid reservoir, or an I.V. bag 108 containing a volume of fluid 110, a length of fluid administration tubing 112, an in-line heater 114, a delivery pump 116, an I.V. cannula or needle 118, and a patient 120. The fluid administration system additionally comprises a controller 122, a heater power/control line 124, a delivery pump power/control line 126, a temperature probe 128, and a temperature feedback line 130. The fluid administration system may optionally comprise a drip chamber 142, an injection port 222 and an adjustable clamp 224.

Referring to FIG. 1, fluid 110 from the fluid reservoir 108 travels, via the tubing 112, through the optional drip chamber 142, to the in-line heater 114 where it is heated. From the in-line heater 114, the fluid 110 travels via the tubing 112 to the delivery pump 116 where it is pumped at a set flow rate. From the delivery pump 116, the fluid 110 travels, via the tubing 112, through the optional injection port 222 and the adjustable clamp 224, to the I.V. cannula 118 that is inserted into the patient 120. Thus, the patient 120 receives the fluid 110. The temperature probe 128 is inserted into the I.V. tubing 112, near the I.V. cannula 118, so that it can sense the temperature of fluid 110, and is connected to the controller 122 through the temperature feedback line 130. The controller 122 is also connected to the in-line heater 114 and the delivery pump 116 through the heater power/control line 124 and the delivery pump power/control line 126, respectively.

The operator sets the flow rate of the fluid 110 at the controller 122. The controller 122 transmits power and flow rate commands to the delivery pump 116 through the delivery pump power/control line 126. The operator also sets the temperature of the fluid 110 at the controller 122. The operator specifies the temperature of the fluid 110 to be administered to the patient 120. The fluid temperature and/or flow rate could also be pre-set or automatically set without requiring operator intervention. The controller 122 transmits power and temperature adjustment commands to the in-line heater 114 through the heater power/control line 124. The temperature probe 128 measures the temperature of the fluid 110 immediately prior to delivery of the fluid 110 to the patient 120. This temperature information is sent through the temperature feedback line 130 to the controller 122 where it is processed. The controller 122 transmits temperature adjustment commands to the in-line heater 114 to maintain the selected fluid temperature at the patient 120. In this manner, the fluid administration system compensates for temperature losses in the fluid administration tubing 112 and assures the patient 120 will receive fluid 110 at the specified temperature. Note that the temperature probe 128 may be a standard commercial thermocouple, thermister or other temperature-measuring device. The delivery pump 116 is optional and the system could work as well using standard gravity feed.

Figure 2:
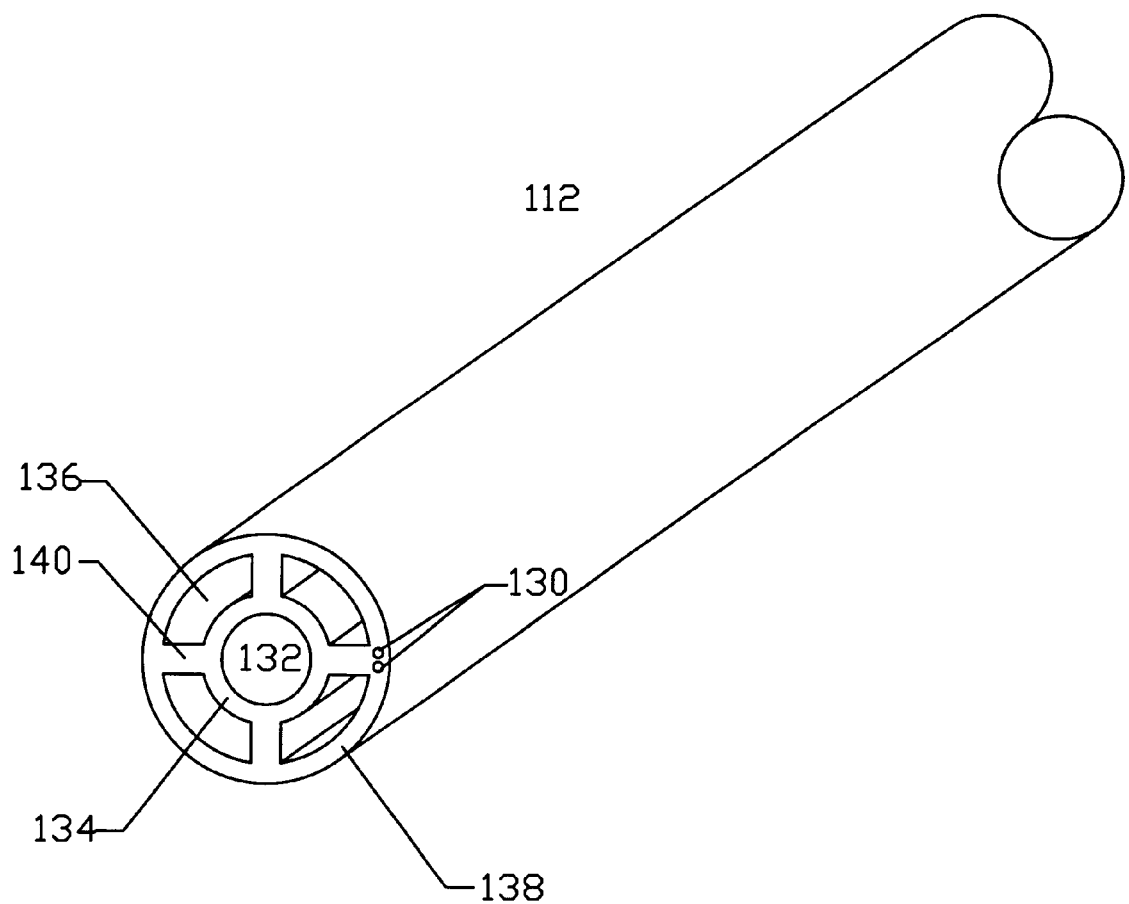
FIG. 2 shows a length of tubing used for fluid administration. The tubing includes a through lumen for fluid administration and four outer lumens.

FIG. 2 illustrates one embodiment of the length of fluid administration tubing 112 of the present invention. The tubing 112 is circular in cross-section and comprises a through lumen 132, an inner wall 134, a plurality of outer lumens 136, an outer wall 138 and a plurality of webs 140. Optionally, the tubing 112 comprises the temperature feedback line 130. The warmed fluid 110 to be administered to the patient 120 travels through the through lumen 132. The outer lumens 136 insulate the through lumen 132 from the ambient temperature and help to reduce the fluid temperature losses in the fluid administration system. The tubing 112 can be extruded from plastic such as polyvinyl chloride, chlorinated polyvinyl chloride, polyethylene, polypropylene, polyurethane and the like. Typically, the plastic is uncolored and transparent to allow for visualization of the fluid. The tubing 112 may be rigid or flexible. Ultraviolet light resistant additives or blue colorants may also be added to compensate for color changes that occur during gamma or E-beam sterilization. The tubing 112 can also be a simple single lumen tube.

Referring to FIGS. 1 and 2, the temperature feedback line 130 can optionally be embedded in the fluid administration tubing 112. The temperature feedback line 130 may be fabricated from copper, steel or other conductive metal. Via a connection (not shown) at or near the in-line heater 114, the temperature feedback information is transmitted on the heater power/control line 124 to the controller 122 where the information is used to control the heating of the fluid 110. This operates the same and produces the same results as having a physically independent temperature feedback line 130 as shown in FIG. 1. However, embedding the temperature feedback line 130 in the fluid administration tubing 112 results in a simpler system.

Additional features of the system could include pressure, optical or flow sensors to warn the controller 122 if the fluid administration reservoir 108 is empty. Such a system could cause controller 122 to shut off delivery pump 116 so as not to cause damage to the system or pump air into the patient 120.

Figure 3:
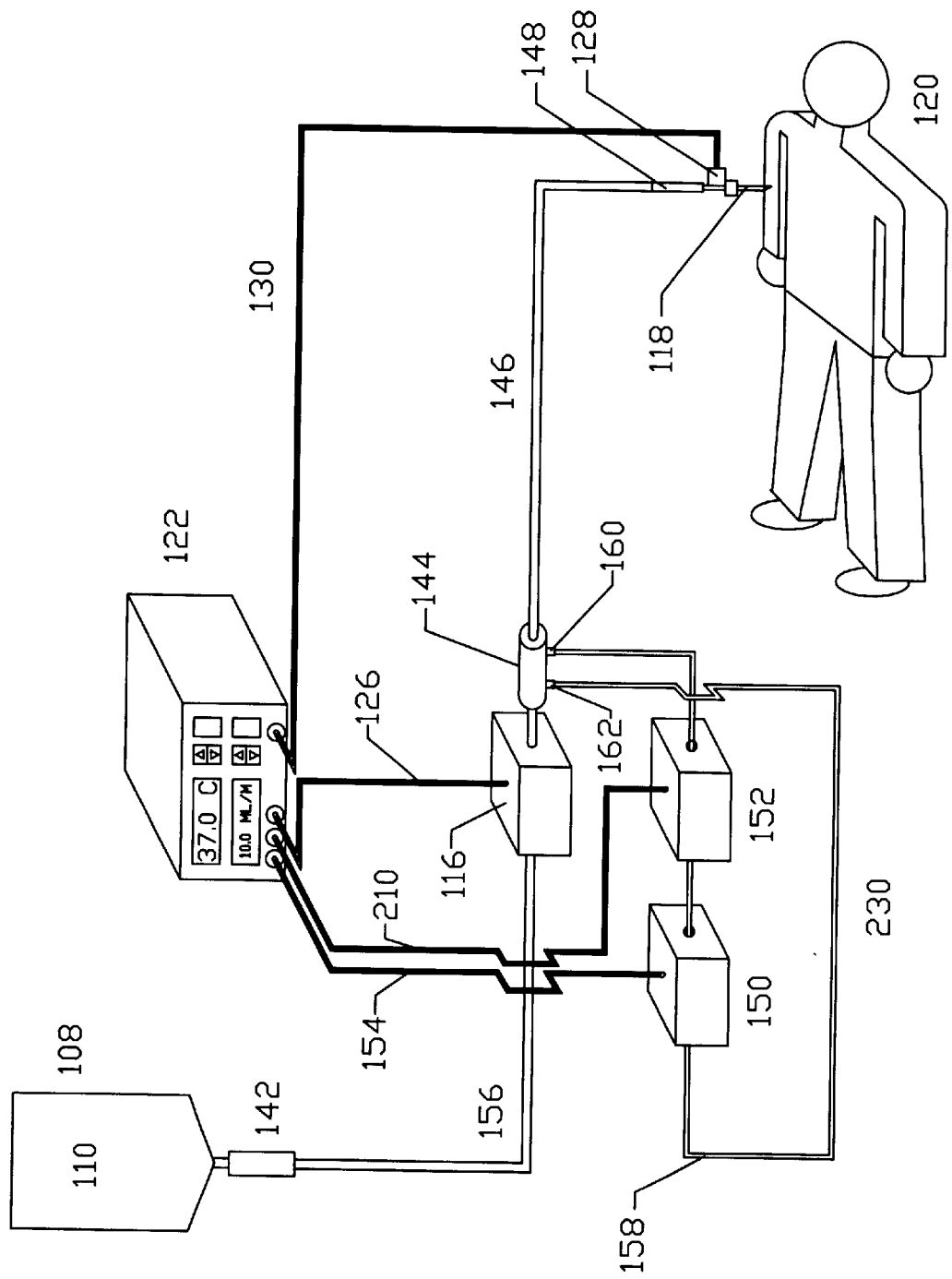
FIG. 3 shows a system for fluid administration utilizing the distributed heat exchange elements of the invention.

FIG. 3 shows a preferred embodiment of the fluid administration system. In this embodiment, the fluid 110 to be administered to the patient is not heated with an isolated in-line heater, but is heated by distributed temperature transfer from a warmed heat exchange fluid. The fluid administration system of FIG. 3 comprises the fluid reservoir 108, the optional drip chamber 142, a length of tubing 156, the delivery pump 116, a heat exchange manifold 144, a length of heat exchange fluid administration tubing 146, a flow shunt 148, the I.V. cannula 118, and the patient 120. The heat exchange manifold 144 comprises an input port 160 and an output port 162. The fluid administration system additionally comprises the controller 122, a heat exchange fluid heater 150, a circulating pump 152, a length of circulation tubing 230 and a volume of heat exchange fluid 158. The fluid administration system additionally comprises a heat exchange power/control line 154, a circulating pump power/control line 210, the delivery pump power/control line 126, the temperature probe 128, and the temperature feedback line 130. Optionally, the fluid administration system could comprise the injection port 222 and the clamp 224 as shown in FIG. 1.

Referring to FIG. 3, the fluid 110 from the I.V. bag 108 travels through the optional drip chamber 142 to the delivery pump 116 via the tubing 156. The fluid 110 is pumped from the delivery pump 116 to the heat exchange manifold 144 via the tubing 156. From the heat exchange manifold 144, the fluid 110 travels to the flow shunt 148 via the heat exchange fluid administration tubing 146. The fluid 110 leaves the flow shunt 148 and enters the I.V. cannula 118 that is inserted into the patient 120. Thus, the patient 120 receives the fluid 110.

The temperature probe 128 is located at, or near, the I.V. cannula 118 and is connected to the controller 122 through the temperature feedback line 130. The temperature probe 128 is located to sense the temperature of the fluid 110, just before the fluid 110 is delivered to the patient 120. The temperature probe 128 may have a sensing element touching the fluid 110 or it may be separated from the fluid 110 by a layer of adequately heat conductive material such as metal or thin layer of plastic.

The controller 122 electrically connects to the delivery pump 116 through the delivery pump power/control line 126. The controller 122 also electrically connects to the heat exchange fluid heater 150 through the heat exchange power/control line 154. The controller 122 electrically connects to circulation pump 152 through the circulation pump power/control line 210. The heat exchange fluid heater 150 connects to the circulation pump 152 and the heat exchange manifold 144 through tubing 156. The circulating pump 152 also connects to the heat exchange manifold 144 through tubing 156.

The fluid 110 travels through the optional drip chamber 142 to the delivery pump 116 where it is pumped through the heat exchange manifold 144, the flow-shunt 148, and the I.V. cannula 118 to the patient 120. The operator sets the flow rate at the controller 122. The controller 122 transmits power and flow rate commands through the delivery pump power/control line 126 to the delivery pump 116. The delivery pump 116 is optional and the apparatus would work as well with standard gravity feed.

The fluid 110 is not heated by an in-line heater as was described in an earlier embodiment. Within this fluid administration system there exists a closed heat exchange loop that is distributed along at least a portion of the length of the heat exchange fluid administration tubing 146. The operator sets the temperature of the fluid 110 to be delivered to the patient 120 at the controller 122. The controller 122 transmits temperature information to the heat exchange fluid heater 150, through the heat exchange power/control line 154, which heats the heat exchange fluid 158. The heat exchange fluid 158 could be stored in a reservoir (not shown) or pre-filled within the circulation tubing 230.

Referring to FIG. 3, the heat exchange fluid 158 enters the circulating pump 152 and is pumped to the heat exchange manifold 144 through the heat exchange manifold input port 160 via circulation tubing 230. The controller 122 transmits flow rate information through the circulating pump power/control line 210 to the circulating pump 152 to control the flow rate of the heat exchange fluid 158. The heat exchange fluid 158 travels, via the heat exchange fluid administration tubing 146, separately, parallel and adjacent to the fluid 110 in order to transfer heat to the fluid 110. At the flow shunt 148, the heat exchange fluid 158 is directed back around, or shunted, and flows, via the heat exchange fluid administration tubing 146, separately, parallel and adjacent to the fluid 110 but in the opposite direction. Again, the heat exchange fluid 158 transfers heat to the fluid 110. When the heat exchange fluid 158 enters the heat exchange manifold 144, it passes through the heat exchange manifold output port 162 and enters the heat exchange fluid heater 150 via circulation tubing 230. Once in the heat exchange fluid heater 150, the heat exchange fluid 158 is reheated and delivered to the circulating pump 152 to circulate through the heat exchange loop again. In this manner, the fluid 110 is heated to the specified temperature.

Figure 4:
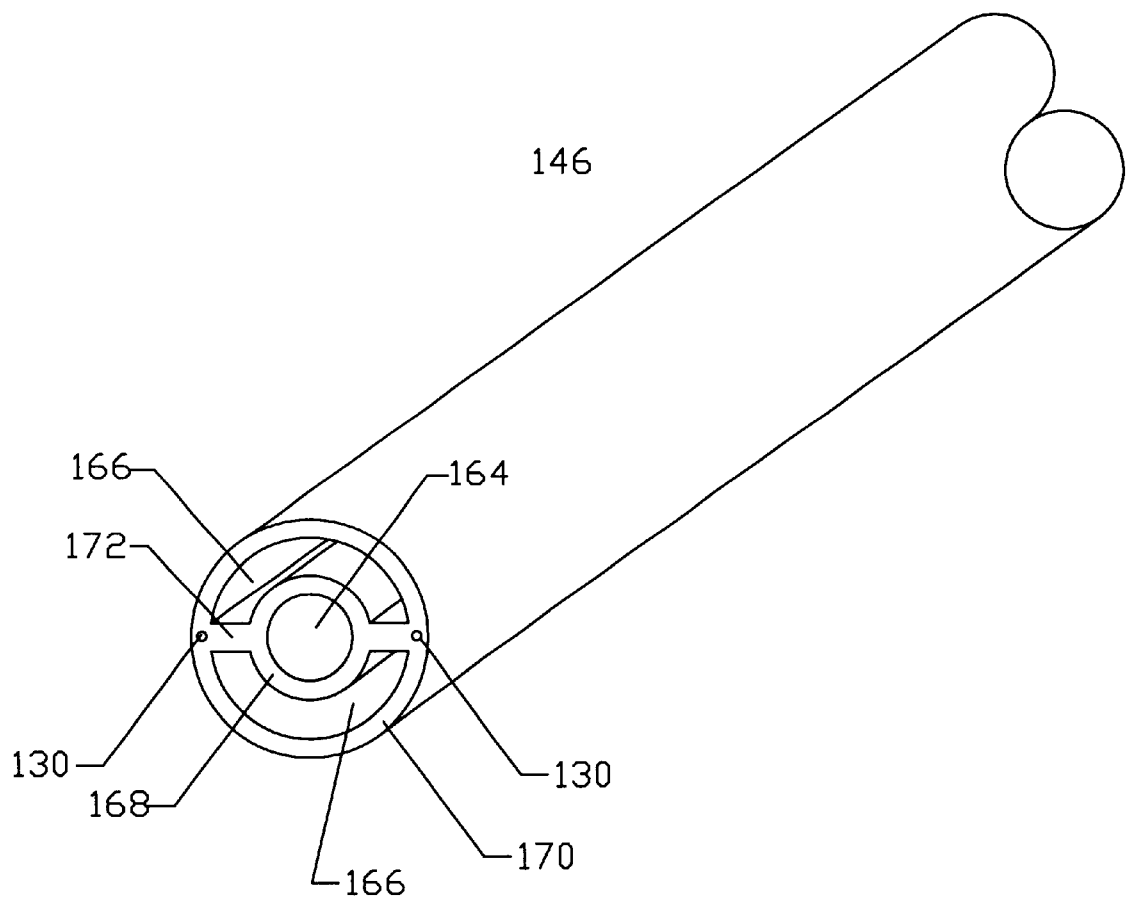
FIG. 4 shows a length of tubing used for fluid administration. The tubing includes a through lumen for fluid administration and two outer lumens for carrying fluids or for insulation.
Figure 6:
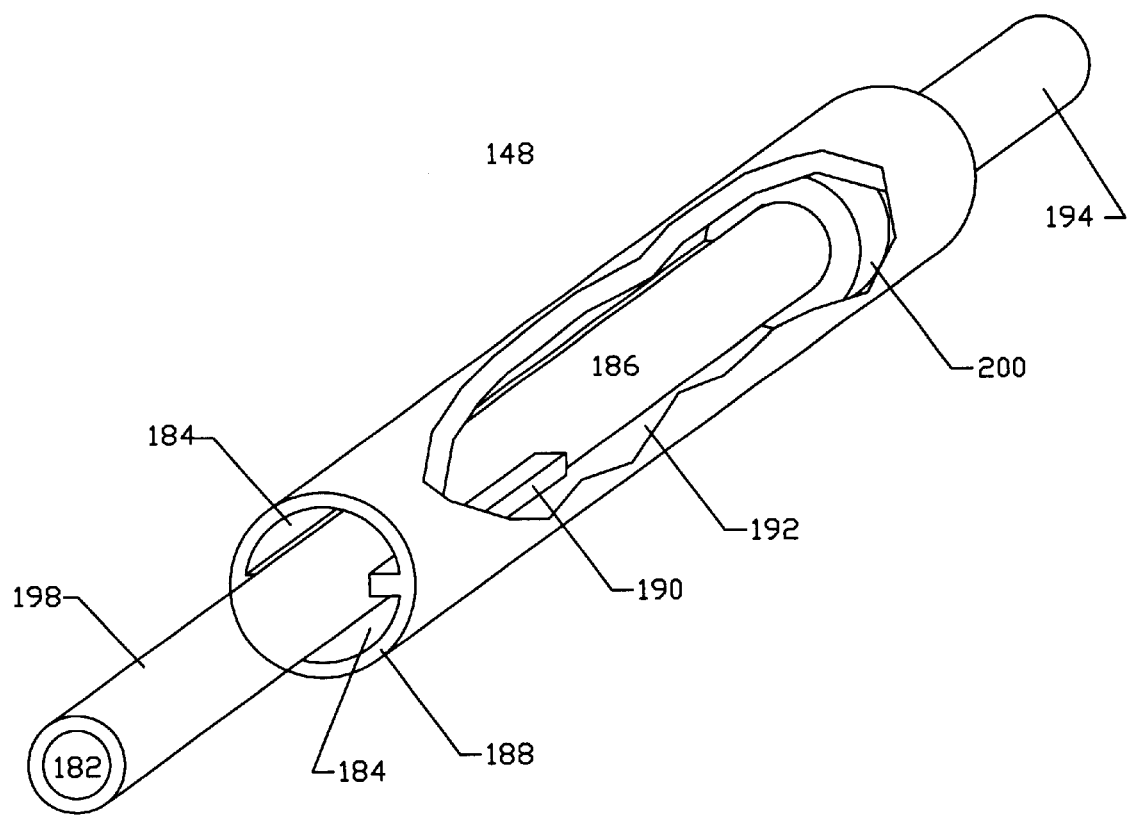
FIG. 6 shows a cutaway view of the flow shunt located at one or more ends of the distributed heat exchange fluid administration tubing.

To further clarify the heat exchange process, refer to FIGS. 4, 5 and 6. FIG. 4 illustrates the length of heat exchange fluid administration tubing 146. The heat exchange administration tubing 146 is circular in cross-section and comprises a through lumen 164, a set of at least two outer lumens 166, an inner wall 168, an outer wall 170, and a set of at least two webs 172. Optionally the tubing 146 comprises the temperature feedback line 130.

FIG. 5A illustrates the longitudinal cross-section and FIG. 5B illustrates the lateral cross-section of the heat exchange manifold 144. The heat exchange manifold 144 comprises the input port 160, the output port 162, a through lumen 172, an input chamber 174, an output chamber 176, a set of webs 202, a delivery fluid administration tubing connector 178, and a heat exchange fluid administration tubing connector 180. The input chamber 174 is separated from the output chamber 176 by the webs 202.

FIG. 6 shows a cross-sectional cut away view of the flow shunt 148. The flow shunt 148 comprises a through lumen 182, a set of at least two outer lumens 184, an inner wall 186, an outer wall 188, a set of at least two ribs 190, a return chamber 192, a flow shunt connector 198, a flow diverter 200 and a through lumen extension 194. The ribs 190 that separate the outer lumens 184 from each other are broken in the middle of the flow shunt 148 to create the return chamber 192.

Referring to FIGS. 3, 4, and 5, the warmed heat exchange fluid 158 is pumped through circulation tubing 230 into the heat exchange manifold input port 160 and enters the input chamber 174. The heat exchange fluid administration tube 146 is connected to the heat exchange manifold 144 at the heat exchange fluid administration tubing connector 180. The through lumen 172 of the heat exchange manifold 144 and the through lumen 164 of the heat exchange fluid administration tubing 146 are aligned. Likewise, the output chamber 176 of the heat exchange manifold 144 aligns with one of the outer lumens 166 of the heat exchange fluid administration tubing 146 and the input chamber 174 of the heat exchange manifold 144 aligns with the other outer lumen 166 of the heat exchange fluid administration tubing 146. Similarly, the heat exchange manifold 144 is connected to the tubing 156 through the delivery fluid administration tubing connector 178 and a delivery fluid lumen of the tube 156 is aligned with the through lumen 172 of the heat exchange manifold 144. The tubing 156 can simply be tubing with a minimum of one lumen, which carries fluid, the fluid administration tubing 112 shown in FIG. 2, or the heat exchange fluid administration tubing 146 shown in FIG. 4.

Again referring to FIGS. 4, 5, and 6, the warmed heat exchange fluid 158 exits the heat exchange manifold input chamber 174 and enters one of the outer lumens 166 of the heat exchange fluid administration tube 146. The through lumens 172 and 164 of the heat exchange manifold 144 and the heat exchange fluid administration tubing 146, respectively, transport the delivery fluid 110. As the delivery fluid 110 flows through the through lumen 164 of the heat exchange fluid administration tubing 146, the warmed heat exchange fluid 158 flows through one of the outer lumens 166. Heat transfer occurs from the heat exchange fluid 158 to the delivery fluid 110 through the inner wall 168 of the heat exchange fluid administration tubing 146 along the length of the heat exchange fluid administration tubing 146. The heat exchange fluid administration tubing 146 is connected to the flow shunt 148 through the flow shunt connector 198. The through lumen 164 of the heat exchange fluid administration tubing 146 aligns with the through lumen 182 of the flow shunt 148. Likewise, the outer lumens 166 of the heat exchange fluid administration tubing 146 align with the outer lumens 184 of the flow shunt 148. When the fluids 110 and 158 reach the flow shunt 148, the delivery fluid 110 passes through the flow shunt 148 through lumen 182. The I.V. cannula 118 and the temperature probe 128 are connected to the flow shunt 148 at the flow shunt through lumen extension 194. The delivery fluid 110 at the specified temperature flows into the I.V. cannula 118 where it is delivered to the patient 120.

Referring to FIG. 6, the heat exchange fluid 158 enters one of the flow shunt outer lumens 184 through the flow shunt connector 198 and from there the heat exchange fluid 158 is diverted by flow diverter 200 into the return chamber 192 where it is sent back through the other outer lumen 184 of the flow shunt 148.

Referring to FIGS. 3, 4, and 5, the heat exchange fluid 158 flows in the other outer lumen 166 of the heat exchange fluid administration tubing 146, adjacent to the through lumen 164 of the heat exchange fluid administration tubing 146 carrying the delivery fluid 110. Again, heat is transferred from the heat exchange fluid 158 across the inner wall 168 of the heat exchange fluid administration tubing 146 to the delivery fluid 110. The return heat exchange fluid 158 travels through the outer lumen 166 of the heat exchange fluid administration tubing 146 and enters the heat exchange manifold 144 through the heat exchange fluid administration tubing connector 180. The heat exchange fluid 158 has lost much or all of its warmth and travels from the heat exchange manifold 144 through the heat exchange manifold output port 162 to the heat exchange fluid heater 150 via circulation tubing 230. Circulation tubing 230 is tubing with at least one lumen. The tubing 230 can be extruded from plastic such as polyvinyl chloride, chlorinated polyvinyl chloride, polyethylene, polypropylene, polyurethane and the like and may comprise an insulation layer. Typically, the plastic is uncolored and transparent to allow for visualization of the fluid. The tubing 230 may be rigid or flexible. Ultraviolet light resistant additives or blue colorants may also be added to compensate for color changes that occur during gamma or E-beam sterilization. The tubing 230 can also be a simple single lumen tube.

Referring to FIG. 3, the controller 122 sends heating commands to the heater 150 according to the information the controller 122 received from the feedback temperature line 130. In this manner, the heat exchange fluid 158 circulates along the length of the heat exchange fluid administration tubing 146 and warms the delivery fluid 110 for the patient 120.

Figure 7:
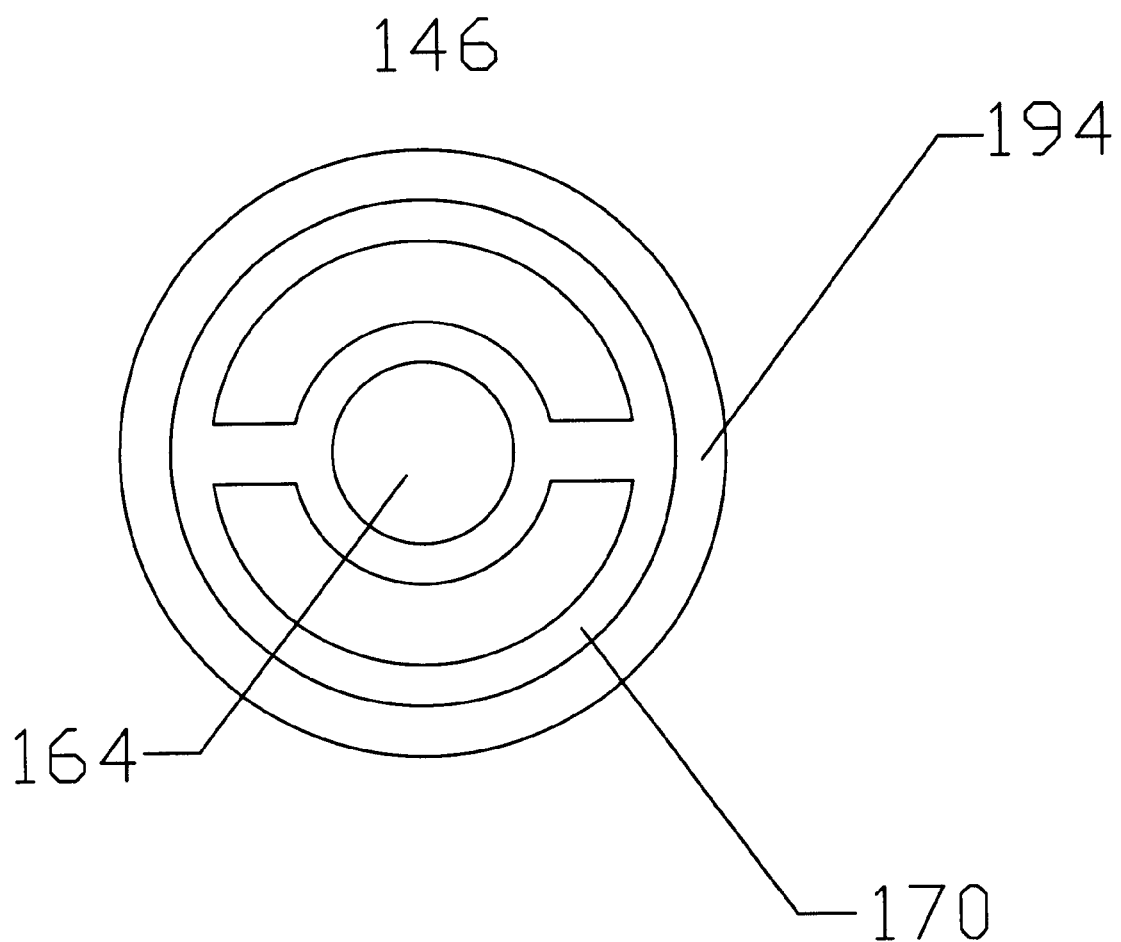
FIG. 7 shows a lateral cross-section of another embodiment of distributed heat exchange fluid administration tubing with an extra insulation layer on the exterior.

FIG. 7 shows a different embodiment of the heat exchange fluid administration tubing 146. In this embodiment, the outer wall 170 of the heat exchange tubing 146 is covered with a layer of insulation 194. The insulation 194 reduces the heat loss in the heat exchange fluid 158 and in the delivery fluid 110 to the ambient air. The insulation could be made of polyurethane foam or air-spaced tubing, for example.

Additionally the fluid administration tubing 112 shown in FIG. 2 could also have an insulation layer 194 like the one shown in FIG. 7.

Figure 8:
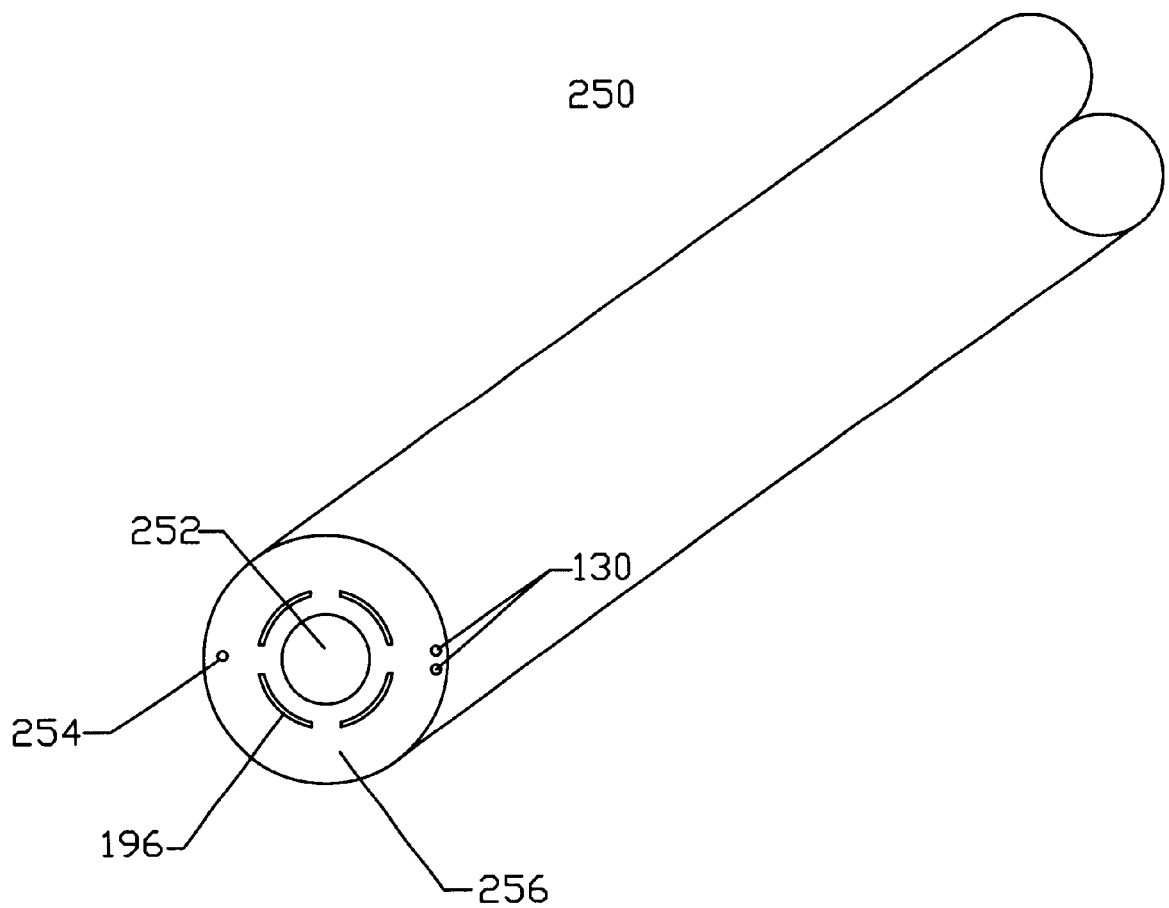
FIG. 8 shows a length of tubing used for fluid administration. The tubing includes a resistive heating element.

FIG. 8 shows yet another embodiment of the apparatus for heating fluid 110. The heat exchange apparatus is a length of warming fluid administration tubing 250. This length of warming fluid administration tubing 250 replaces the in-line heater 114 shown in FIG. 1. The warming fluid administration tubing 250 can also replace the heat exchange fluid loop shown in FIG. 3. The warming fluid administration tubing 250 comprises at least one resistive heating element 196, a through lumen 252, a tubing wall 256. Optionally, the warming fluid administration tubing 250 may comprise the temperature feedback line 130 and at least one electrical lead 254. Additionally, the warming fluid administration tubing 250 may comprise outer lumens for insulation or a layer of insulating material surrounding the outside of at least a portion of the tubing.

The resistive heating element or elements 196 are disposed adjacent to the through lumen 252 and are embedded in the wall 256 of the tubing 250. The resistive heating element or elements 196 are warmed by completing a circuit through the elements 196 and optional electrical lead 254 and creating electrical circuit losses, which occur as heat. If the optional electrical lead 254 is not used, the circuit may be completed by electrically connecting at least two resistive heating elements 196. The warm resistive element or elements 196 transfer heat to the delivery fluid 110 through the tubing wall 256. Referring to FIG. 1, the resistive heating elements 196 are electrically connected to the controller 122 by the heater power/control line 124.

Referring to FIG. 2, similarly, the resistive heating element 196 could be embedded in the outer wall 138 of the fluid administration tubing 112 and heat fluids in one or both lumens 132 and 136.

The resistive element 196 can be fabricated from material such as, but not limited to, nickel-chromium wire or other high-resistance metal. Electrical lead 254 may be fabricated from any low resistance metal such as copper, steel and the like. The metal may be formed into the tubing 250 or 112 during the extrusion process or placed in a special lumen during a secondary operation. Note that the metal heating elements 196 may be fully embedded in the plastic walls 256, 134 or 138, partially embedded in the plastic or fully exposed to the through lumen 252 or 132, respectively. The metal heating elements 196 may be circular, I-beam, flat, partial cylinders or other shapes.

At least a portion of the fluid administration system will be sterilized prior to use. Such sterilization shall include methods such as ethylene oxide and gamma radiation. The portion that is sterilized shall include, at least, all components, which could come in direct contact with the fluid 110 being administered to the patient.

The present invention solves a problem where patients are not currently given medical temperature therapy because of inconvenience and cost. The invention provides for a cost-effective, rapidly implemented system of providing fluids that are warmed to the correct temperature to patients. This is especially important in the emergency and surgical setting where patients lose large amounts of heat and their recovery is impeded by the onset of untreated hypothermia.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes which come within the meaning and range of equivalency of the claims are to be embraced within their scope.

I claim:

1. An apparatus adapted for fluid administration to a patient comprising: a reservoir containing a volume of fluid to be administered to a patient; a volume of warmed heating fluid; and a length of fluid administration tubing comprising an I.V. fluid lumen, and a heating lumen, wherein the heating lumen runs parallel to the I.V. fluid lumen and wherein I.V. fluid flows in the I.V. fluid lumen and a warmed heating fluid flows in the heating lumen, and wherein the warmed heating fluid heats the I.V. fluid along substantially the length of the fluid administration tubing, and further comprising at least one resistive heating element disposed within and axially along the fluid administration tubing, wherein the heating element runs parallel to the I.V. fluid lumen.

2. The apparatus of claim 1, further comprising:
a second heating lumen in said fluid administration tubing running parallel to said I.V. fluid lumen; and
wherein the flow shunt shunts the warmed heating fluid from the heating lumen to the second heating lumen.

3. The apparatus of claim 1 which further comprises:
a temperature probe;
a heater controller; and
a feedback line to the heater controller from said temperature probe.

4. The apparatus of claim 1 further comprising insulation.

5. The apparatus of claim 2 further comprising a heating fluid source comprising a heater, a pump and a length of heating tubing wherein the heating source heats the heating fluid.

6. The apparatus of claim 5 further comprising a heat exchange manifold operably connected to said heating lumens and said heating loop, wherein the heat exchange manifold connects the heating lumens to the heating fluid source.

7. The apparatus of claim 3 wherein the temperature probe is located substantially near an I.V. cannula, wherein an end of the I.V. cannula is inserted into the patient, and wherein the temperature probe monitors a temperature of the I.V. fluid.

8. The apparatus of claim 7 further comprising temperature feedback electrical lines that are embedded in the fluid administration tubing, wherein the temperature feedback electrical lines connect the temperature probe to an external controller.

9. The apparatus of claim 1 wherein the heating lumen is located radially exterior to the I.V. fluid lumen in the fluid administration tubing.

10. The apparatus of claim 1 wherein the warmed heating fluid is injected into the heating lumen of the fluid administration tubing by a heating fluid source comprising a pump, a heater, and a controller.

11. A method of delivering temperature controlled fluids to a patient comprising the steps of:
providing a volume of I.V. fluid to be administered to a patient;
delivering said volume of I.V. fluid to the patient through a length of fluid administration tubing that comprises an I.V. fluid lumen and a heating lumen, wherein the volume of I.V. fluid is delivered to the patient through the I.V. fluid lumen;
heating a heating fluid to generate a warmed heating fluid, wherein the warmed heating fluid is heated by a heating fluid source, and further by using a resistive heating elements disposed parallel to said heating lumen; and
circulating the warmed heating fluid through the heating lumen of the fluid administration tubing, wherein the heating fluid heats the I.V. fluid along substantially the length of the fluid administration tubing.

12. The method of claim 11 wherein circulating the warmed heating fluid comprises pumping the warmed heating fluids through the heating lumens.

13. The method of claim 11 further comprising measuring a temperature of said I.V. fluid at or near the patient and using the temperature to control the heating of the heating fluid.

14. The method of claim 12 wherein the step of pumping said heating fluid into said heating lumen further comprises connecting a heating fluid source substantially near an end of the fluid administration tubing away from the patient.

* * * * *